United States Patent [19]

Ellis et al.

[11] Patent Number: 4,824,671

[45] Date of Patent: Apr. 25, 1989

[54] IN VITRO METHOD FOR PRODUCING INFECTIVE BACTERIAL SPORES AND SPORE-CONTAINING INSECTICIDAL COMPOSITIONS

[75] Inventors: Beth-Jayne Ellis; Frederick Obenchain, both of Manassas, Va.; Raj Mehta, King of Prussia, Pa.

[73] Assignee: Reuter Laboratories, Inc., Va.

[21] Appl. No.: 843,163

[22] Filed: Mar. 24, 1986

[51] Int. Cl.$^4$ .................... A01N 63/00; C12N 3/00; C12N 11/02; C12R 3/00

[52] U.S. Cl. .................... 424/195.1; 424/95; 424/93; 435/242; 435/832; 435/176

[58] Field of Search ............ 435/242, 244, 246, 253, 435/259, 170, 176, 177, 832; 424/92, 93, 95, 195.1

[56] References Cited

U.S. PATENT DOCUMENTS

| | | | |
|---|---|---|---|
| 3,503,851 | 3/1970 | Srinivasan | 435/242 |
| 3,790,665 | 2/1974 | Glass et al. | 424/92 |
| 3,950,225 | 4/1976 | Skole et al. | 435/242 |
| 4,626,508 | 12/1986 | Steinkraus | 435/242 |
| 4,661,351 | 4/1987 | Gago et al. | 435/253 |

OTHER PUBLICATIONS

Costilow, R. N. et al., Physiological Studies of an Oligosporogenous Strain of *Bacillus Popolliae*; *Appl. Microbiol.*, vol. 22, No. 6, (1971), pp. 1076-1084.

Sharpe, E. S. et al.; Characteristics of a New Strain of *Bacillus Popilliae* Sporogenic in Vitro; *Appl. Microbiol.* vol. 19, No. 4, (1970); pp. 681-688.

St. Julian, G. et al.; Preparation and Characterization of Intact and Free Spores of *Bacillus Popilliae* Dutky; *Can. J. Microbiol.* vol. 13 (1967); pp. 279-285.

Haynes, W. C. et al; Sporulation of *Bacillus Popilliae* in Liquid Medium as Affected by Kind of Carbon and Method of Sterilization; *Can. J. Microbiol.*, vol. 18 (1972); pp. 515-518.

Primary Examiner—Elizabeth C. Weimar
Attorney, Agent, or Firm—Darby & Darby

[57] ABSTRACT

Disclosed are insecticidal compositions for controlling Scarabaeide comprising an effective amount of sporangium-free spores of pathogens that cause milky disease in said Scarabaeide. Also disclosed is a method for producing infective milky disease bacillus spores in vitro in liquid media containing starch, trechalose, yeast extract, $K_2HPO_4$, and $CaCO_3$ during the vegetative growth stage and $MnSO_4$ and optionally an ion-exchange resin as sporulation adjuvants.

19 Claims, 3 Drawing Sheets

IN VITRO METHOD FOR PRODUCING INFECTIVE BACTERIAL SPORES AND SPORE-CONTAINING INSECTICIDAL COMPOSITIONS

FIELD OF THE INVENTION

This invention relates to novel insecticidal compositions comprising in vitro-produced spores of bacteria that cause milky disease in scarabaeid larvae and to improved methods for making such compositions.

BACKGROUND OF THE INVENTION

The most effective existing method for controlling Scarabaeidae, such as the Japanese beetle, comprises infecting the larvae with host-specific bacteria that cause milky disease in these larvae. Milky disease is lethal to the larvae, but harmless to other species of animals or plants. Known milky disease bacteria include, but are not limited to, the various varieties of *Bacillus popilliae* (including the varieties popilliae, lentimorbus, melolonthae, rhopaea, N.Z. Type I, N.Z. Type II, etc.)

The vegetative (rod) stage of these bactieria is not suitable for use in insecticidal preparations. Rods are sensitive and do not survive under the conditions associated with insecticide application methods or under those prevailing in the fields. By contrast, the spores of these bacteria are very resistant to adverse environmental conditions and remain viable (and infective) in the field after application (in liquid, powder, granular, or bait formulations) and for prolonged period of time thereafter.

Because of the high mortality rate of milky disease, the host-specificity of the milky disease pathogens and the absence of the type of adverse environmental impact that usually accompanies use of chemical pesticides, the milky disease spores are particularly suitable for use in pesticidal compositions. However, various difficulties in obtaining effective spores, particularly in large and economically attractive quantities, have prevented such pesticides from gaining wide acceptance.

Many investigators have failed to obtain substantial sporulation of *B. popilliae* and other milky disease bacteria in vitro, Dutky first proposed a method for producing *B. popilliae* spores in vivo. This method, described, e.g., in U.S. Pat. No. 2,293,890, involves injecting live Japanese beetle larvae with viable *B. popilliae* spores (themselves obtained from the hemolymph of diseased larvae), waiting for the disease to develop, drying and powdering the diseased larvae, and applying the resulting material in the field.

It is evident that this in vivo method is extremely tedious, costly, and labor-intensive. Moreover, it can produce only limited amounts of *B. popilliae* product, both because the quantity of spores obtained as a percentage of the larvae mass is small, and because scarabaeid larvae can be obtained or grown only during certain months (March to May and August to October).

To satisfy the recognized need for an alternative source of milky disease spores, investigation turned to in vitro methods. Unfortunately, only limited sporulation of milky disease bacteria has been reported in vitro. Although large numbers of vegetative cells can be produced in artificial (liquid or solid) media, the average degree of sporulation does not usually exceed about 10–30% and the spore infectivity has been reported to be either substantially impaired (such that it would not be commercially useful) or nonexistent: see, M. G. Klein, "Advances in the Use of *B. popilliae* for Pest Control" in *Micr. Contr. of Pests and Plant Diseases*, Burgess, H.D. (Editor) 1981 Academic Press, pp. 184–192.

St. Julien and L. A. Bulla, Jr. *Current Topics in Comparative Pathobiology*, T. C. Cheng (Editor) 1973, G., Vol. 2, Academic Press, pp 57–87 report that as high as 20% sporulation occurs in a population of NRRL B-2309M colonial cells in solid medium formulated with yeast extract, the ingredients of Mueller-Hinton medium (1%), trehalose, and phosphate. Mueller-Hinton medium contains a very low amount (0.15%) of starch. Therefore, the St. Julien and Bulla medium contains only about 0.0015% of starch.

U.S. Pat. No. 3,308,038 of Rhodes et al is directed to a process for inducing in vitro sporulation of NRRLB-2309 substrains of *B. popilliae* to the extent of only 3–5% by (a) culturing vegetative cells for 18–24 hours in shaken flasks (or with 0.15–0.5 vvm aeration) in an aqueous medium containing (on a weight-per-volume basis) 0.2% glucose, fructose or trehalose, 1.5–2.0% yeast extract, and sufficient $K_2HPO_4$ to adjust the pH to 7.2–7.5 (0.3%); (b) transferring the cells to slants or plates containing agar, yeast extract, sodium acetate, and $K_2HPO_4$ to form uncrowded colonies; and (c) culturing the colonies for 42 days until sporulation occurs.

U.S. Pat. No. 3,071,519 of Bonnefoi is directed to a method for producing large number of spores of B. thuringiensis involving culturing a stock of this bacterium in a liquid medium at a pH between 5.5 and 8.5 containing aminated nitrogen and at least one of saccharase, maltose, dextrose and dextrin and, as a trace element, one or more of calcium, zinc, manganese and magnesium until sporulation occurs, and harvesting the spores. However, *B. thuringiensis* is not a milky disease bacterium. Moreover, *B. thuringiensis* has proved to be much easier to grow in vitro than the milky disease bacilli.

U.S. Pat. No. 3,503,851 to Srinivasan is directed to an in vitro method for producing *B. popilliae* spores comprising growing *B. popilliae* in a liquid medium containing yeast extract, glucose, glycerol, sodium chloride, ammonium sulfate, $K_2HPO_4$, $MnSO_4.H_2O$, $CaCl_2$, $ZnSO_4.7H_2O$, $FeSO_4.7H_2O$ and a small amount of a chloroaliphatic compound, such as a chloroacetamide, chloroform or a trichloroethane. The thud obtained sporulation rate is said to be as large as 80%.

First, the use of chloroaliphatic compounds is undesirable for two reasons: (a) these compounds are volatile and would need constant replenishment in an aerated culture medium, which adds to the production costs; and (b) these compounds are toxic—their vapors would present a hazard to plant personnel and residual amounts that would remain in the product, would be released into the environment and contaminate agricultural crops. For these reasons, Srinivasan's process is neither amenable to nor desirable for commercial-scale production.

Second, the strains deposited by Srinivasan are not *B. popilliae*. These strains are reported as having been misidentified in the *Agricultural Handbook*, infra, Table 50, pp 260–261 (citing Srinivasan's patent discussed above) and have been since identified as not *B. popilliae* (*B. megaterium, B. cereus, B. polymyxa*, etc.). The literature also contains other reports of *B. cereus* and *B. polymyxa* being confused with *B. popilliae*.

U.S. Pat. No. 3,950,225 of Skole is directed to a two-stage (fermentation-sporulation) method for *B. popilliae* and *B. lentimorbus*. Vegetative growth is accomplished in a medium containing yeast extract, $K_2HPO_4$, glucose and triptose. The resulting cell mass is then transferred to and incubated in cane sugar refinery animal char waste water as a sporulation medium. The patent contends that a sporulation rate of 100% was obtained by this process but does not give the basis on which this figure was calculated. The patent is silent about spore counts on a per-unit-volume (of culture medium) basis. Furthermore, in the only example, the patent states that a cell mass of 6.5±0.5 g was transferred from 75 ml of vegetative growth medium to 5 liters of waste char water. This represents a more than 66-fold increase in volume, which would be highly impractical on a commercial scale. Finally, the Skole patent contains no infectivity data on the in vitro-produced spores.

Thus, many investigators have published or patented detailed protocols for inducing sporulation of *B. popilliae* in vitro. However, none of these procedures have been found to meet the basic requirements of an efficient process for producing *B. popilliae* spores that would be suitable for large scale production.

These requirements are:

large cell populations should be produced per unit fermentation volume;

a high percentage of the cells should sporulate;

growth and sporulation should occur under conditions amenable to large scale processing;

the resulting spores should be capable of germinating and should be infective.

Currently, *B. popilliae* var. popilliae (which may contain small amounts of the lentimorbus variety) is the only milky disease bacillus that is produced commercially and it is produced only in vivo.

The failure of the prior art to provide an efficient process (especially one adaptable for commercial-size scale-up) for producing milky disease spores in vitro was accompanied (or possibly caused) by certain views about the morphology and properties of milky disease bacilli, and in particular, of *B. popilliae* and its varieties. These views are widely held by those skilled in the field as evidenced by numerous references in the literature and constitute the "accepted wisdom" in the field.

*B. popilliae* is universally characterized in the literature as an obligate insect pathogen formed in a swollen sporangium that do not autolyse to release a free spore (see. e.g., R. J. Milner, infra, p. 46). This bacterium is catalasenegative and unable to grow in nutrient broth. It is considered to have extremely fastidious requirements for growth.

The accepted view in the literature about *B. popilliae* spores is that they are almost always retained in a sporangium except in rare instances when the bacilli are grown on solid media in vitro and extremely rarely in vivo. Thus, the appearance of a sporangium is accepted as an important marker for identification of the species. In fact, well recognized investigators have stated that spores grown in liquid culture that doe not have a sporangium are not *B. popilliae.* See generally, the Agriculture Handbook, No. 427, R. E. Gordon, et al (Agricultural Research Service, U.S.D.A., 1973) and R. J. Milner, "Identification of the *Bacillus popilliae* Group of Insect Pathogens" in *Micr. Contr. of Pests and Plant diseases,* Burges, H. D. (Editor) 1981 Academic Press, pp. 45–59. Thus, even if investigators had observed naked (sporangium-free) milky disease spore in media other than those containing acetate, they would not have identified it as such. Sharpe, E. S. et al 1984 *Appl. Microbiol.* 19(4): 681–688 report the observation of occasional free spores in sporulating colonies (i.e. on solid media) of B. popilliae strain NRRL-B-2309M. The same investigators obtained marginal results in terms of in vitro rate of sporulation and—most significant—extremely poor infectivity on assay. The results of their per os infectivity tests (in which the soil was inoculated with $30\times10^6$ spores per gram) were negative. These results prompted the investigators to state:

> Apparently, in vitro spores of *B. popilliae* B-2309M are unable to infect Japanese beetle larvae through the natural pathway, the insect gut. [Sharpe et al, supra, at p. 686]

R. G. Milner, supra reports that the spore and parasporal body can be released from the sporangium by ultrasonics for the purpose of studying the details of the spore surface structure, but this does not involve naked spore directly harvested from liquid culture media.

Another proposition that is widely accepted in the field is that a bioassay, in which *B. popilliae* (or any milky disease spore) is administered to scarabaeid larvae by injection, provides a reliable test for the infectivity of the spores. This injection bioassay has been found to require a lower dose level for infection than those required in bioassays in which the spore is administered per os (such as the soil inoculation bioassay). Given that per os bioassays are substantially more difficult and time-consuming to perform, the injection assay was adopted as the infectivity indicator of choice. Moreover, spores found to be noninfective by injection have often been reported to be noninfective when administered per os. The converse has not been reported.

All of the observations mentioned above serve to construct in the minds of those skilled in the art the implicit conviction that is spores were not infective when administered by injection, they would not be infective when ad- ministered per os.

In summary, the state of the art (at the time the present invention was made) accepted the above-described statements on the morphology and properties of milky disease bacilli, and in particular of *B. popilliae,* and had not succeeded in efficiently growing *B. popilliae* in vitro on a large scale.

OBJECTS OF THE INVENTION

Accordingly, one object of the present invention is to provide a method of promoting the in vitro sporulation of milky disease bacilli to an extent substantially greater than that achieved by the prior art, especially in terms of yield.

Another object is to provide a method for obtaining large quantities of milky disease bacillus spores, by increasing the efficiency of the in vitro sporulation of these pathogens.

Another object is to provide a method for obtaining large quantities of viable, germinable and infective milky disease spores, especially when these spores are administered per os.

Another object is to provide an insecticidal composition for use in combatting infestations of Scarabaeidae and other susceptible pests in fields, orchards, gardens and containers (potted plants) comprising milky disease spores produced in vitro.

These and other objects of the present invention will be apparent to those skilled in the art in view of the following description, claims and drawings.

SUMMARY OF THE INVENTION

One aspect of the present invention is directed to a method for promoting sporulation of milky disease bacilli in vitro comprising: culturing vegetative cells of said bacilli through the end of the growth phase in a sterilized, aerated, pH-controlled medium comprising yeast extract, a soluble sugar, potassium hypophosphate and calcium carbonate; adding in said medium, as a sporulation adjuvant, manganese sulfate and incubating said cells for a time sufficient for more than about 80% sporulation to occur. The yields obtained by this process for stains that exhibit healthy vegetative growth are at least of the order of about $10^9$ spores/ml of liquid medium in a fermenter.

Preferably, the growth medium also comprises soluble starch as a growth stimulator. Preferably, an adsorbent resin is used as an additional sporulation adjuvant.

Another aspect of the present invention is directed to an insecticidal composition comprising as an active ingredient an insecticidally effective amount of sporangiumfree milky disease spore produced in an in vitro culture.

Preferably, the sporangium-free spore is a mixture of spore from at least two different strains.

Most preferably, the composition of the present invention comprises a mixture of sporangium-free and sporangium-bearing milky disease spore with said sporangiumfree spore having at least a substantial participation in the per os infectivity of such composition. However, the percentage of in vivo spore need not exceed 0.01% of the total spore content, which will represent no more than 0.07% of the spore content of marketed products containing solely in vivo spore.

DETAILED DESCRIPTION OF THE INVENTION

The present invention is described in detail below by reference to specific preferred embodiments. A preferred method for producing naked milky disease spore in vitro is first described followed by a description of the growth and sporulation pattern of *B. popilliae* and of its infectivity.

It will be understood, however, that the present invention is not limited to *B. popilliae* but is applicable to all organisms that cause milky disease in scarabaeid larvae and other insects that can be infected with these organisms. Nor are the compositions of the present invention limited to naked spores as produced by the process described below.

It is very important to observe strict sanitary standards at every stage of culture of milky disease bacteria in order to avoid contamination. For the same reasons, it is important to transfer the vegetative cells frequently, and to subject them to frequent microscopic and biochemical examination as well as viability and infectivity tests.

Strains may be maintained by frequent transfer of vegetative cells, or by aseptic storage of viable spores. thus, for strain maintenance, the conditions for growth and sporulation should be aseptic and for production the conditions of harvesting and lyophilization should be at least sanitary if not aseptic.

In accordance with the present invention, maintenance cultures of milky disease bacilli, are first established. Although any normally sporulating infective strain of milky disease bacillus may be used in the present invention, such as NRRL strains B-2309, B-2309-S, B-2309M, and their infective derivatives, sporulating isolates from NRRL strains B-2309T, B-2524, B-3195, B-3391, and B-4154 and their infective derivatives are preferred. The following strains of *B. popilliae* are particularly preferred: ATCC-53256 (RLI-1182-W), ATCC-53257 (RLI-8015-14G), ATCC-53258 (RLI-D-63) and ATCC-53259 (NRRL-B-2309-Micro-1). Most preferred is ATCC-53256 (RLI-D-1182-W).

Essentially all of the spores resulting from in vitro processes of this invention are sporangium-free as harvested at the end of sporulation. The spores, are within a sporangium, but it autolyses in culture when the spore matures.

When injected in scarabaeid larvae the spores produced in accordance with the present invention have infectivity that is substantially below acceptable levels. In addition, higher doses of spore per injection do not result in higher infectivity (see FIG. 2 and Table I). Quite the contrary, the does response quickly reaches a maximum and then decreases. By contrast, the spores of the present invention are quite infective when administered per os, and higher doses result in higher infectivity (see FIG. 3 and Table II).

Because the prior art tends to regard spores without a sporangium as not milky disease spores, and because these spores are not sufficiently infective by injection, it would be against the accepted wisdom in the field to use such spores in formulating insecticidal compositions or in combatting Scarabaeidae infestations in fields, gardens, orchards, pastures, lawns, or containers.

Maintenance cultures can be established on solid media, as is well-known. Sterile solid J medium, preferably modified to contain about (on a basis of weight of ingredient per volume of medium) 1% tryptone (available, e.g. from Difco, Detroit, Michigan); about 0.5% yeast extract (Difco); about 0.3% $K_2HPO_4$; about 0.2% dextrose; and about 1–2% agar (Difco) in distilled water and modified liquid J-medium containing 1.5% yeast, 0.2% trehalose (or glucose), 0.6% $K_2HPO_4$ and 1.5% agar, are particularly preferred. Trehalose or another soluble sugar may be substituted for dextrose and trehalose is preferred. The medium components should be sterilized, preferably by autoclaving; the sugar is preferably autoclåved separately and added aseptically to the other sterilized medium components.

Incubation of the vegetative maintenance culture takes place at 25°–30° C. and preferably at 28° C. Frequent cell transfers (weekly or even bi-weekly) onto fresh medium are preferred to ensure strain maintenance and help prevent accumulation of deleterious and sporulation-inhibiting substances that might be generated by the bacteria. Long-term strain maintenance is achieved by lyophilization of vegetative cells or, preferably, by aseptic storage of spores.

A liquid (submerged) culture is preferably used to achieve full vegetative growth prior to sporulation induction. The preferred liquid media contain about 0.1–0.2% of a nutrient soluble sugar (preferably 0.1% trehalose, as other sugars, notably glucose, have a marked inhibitory effect on sporulation); about 0.5–1.5 and preferably 1.0% yeast extract (casein hydrolysate can be substituted for at least part of the yeast extract); about 0.1–0.6% $K_2HPO_4$ (0.3% most preferred); about 0.0–0.3% $CaCO_3$ (most preferably 0.2%); and distilled water. Preferably, the liquid growth medium also contains about 0.1–2.0% (preferably 1%) soluble starch. The ingredients should be preferably filter-sterilized and added to $CaCO_3$, which should be previously sterilized by separate autoclaving. Alternately, autoclaving can be used as an overall sterilizing technique, but even in that case, the soluble sugar should be separately autoclaved.

The starting pH of the growth medium should be adjusted to between 6.8 and 8.1 and preferably $7.6\pm0.2$. Salts of additional known essential elements and compounds such as manganese, copper, iron, and zinc can be added but sodium should be avoided as it is known to inhibit vegetative growth in some strains. However, the medium is preferably composed of the ingredients previously described without additional materials. Use of this medium, not only promotes vegetative growth, it also helps attain greater sporulation values and higher infectivity of the resulting spores than those achieved by conventional techniques. Soluble starch is believed to be principally an adsorbent or complexing agent for sporulationtoxic products, i.e., a growth stimulant rather than a nutrient.

Bacterial inoculum is prepared from the maintenance culture preferably in a sample of the submerged culture medium under aseptic conditions. The inoculum is ready for use when cell density is about $1\times 10^7$ to about $1.5'10^9$ and preferably when rods are in log phase growth $1\times 10^9$ rods/ml. This usually takes place overnight (10–24 hrs.), but the rate of growth varies from strain to strain. The inoculum is preferably incubated at 32° C. under aeration or mechanical mixing.

The submerged culture is initiated in a fermenter. An appropriate volume of inoculum (preferably 3–12% of the fermenter working volume) is added to the culture medium. The resulting culture is incubated for about 12–24 hours until completion of the growth phase (as evidenced by the end of population log growth). The preferred incubation conditions are $32°\pm 1°$ C. under continuous mechanical mixing (200–250 rpm) and aeration (0.2–0.5 vvm of sterile air) at a pH of no less than about 6.2 (preferably $7.2\pm 0.2$ for optimum growth). Control of pH, which is important for maximizing cell yields, can be accomplished by addition of HCl or a sodium-free base. The optimum pH value varies from strain to strain but generally falls within the limits given above.

Foaming, which is undesirable, usually occurs at higher mixing speeds and/or air rates. Foaming can be controlled, if necessary, by addition of an appropriate foam-breaking agent, such as HODAG FD-62 (a silicone-based antifoaming agent) from Hodag Chemical Corporation, Skokie, Illinois, or another synthetic antifoaming agent, or vegetable oil, or by mechanical means. If a foam-breaking agent is used, it should be in sterile emulsion or solution form. Three ml/liter of a 5% emulsion of HODAG FD-62 by volume is preferred; it is preferably introduced after fermentation is underway but before foam builds up (usually within 4–6 hours from the onset of fermentation).

The length of the culture period during the growth phase depends on the rate of vegetative cell division, but usually lasts 12–24 hours. The preferred cell density for sporulation is $0.5-1.5\times 10^9$ cells/ml. Although the actual cell density obtained (especially on a large scale) may be slightly less, it compares favorably with the cell density in the hemolymph of grubs, which is usually $1-2\times 10^{10}$ cells/ml.

Manganese sulfate is then added as a sporulation adjuvant to induce and promote sporulation. In addition, an absorbent resin is preferably added especially when the strain has not grown vigorously during the vegetative stage. Both of these additives have been found to promote sporulation and result in germinable and infective spores. Although $MnSO_4$ is preferred, other trace minerals may be added in its place, such as common, mineral salts of iron, zinc, cobalt or nickel, or organic salts of these metals, such as aliphatic carboxylic acid salts (e.g., acetates or propionates). Other ion-exchange and/or adsorbent resins may be used individually or in combination, such as the cationic exchange resins Amberlite IR-120 (Rohm & Haas) cationic exchange resin of styrene-divinylbenzene or Dowex 50 WX4 (Dow Chemical Co.) a copolymer of styrene and divinylbenzene; the anion exchange resins Amberlite IRA-410 (a styrenedivinylbenzene ion exchange resin) or IR-45 (a styrene-divinylbenzene ion exchange resin) (both produced by Rohm & Haas); or the nonionic exchange resin Diaion HP-10 a styrene/divinylbenzene resin (Mitsubishi Chemical Industries in Japan). The nonionic exchange resin Amberlite XAD-7 a copolymer of acrylic ester cross-linked with trimethacrylate functional groups (Rohm & Haas) is most preferred.

$MnSO_4$ may be added in amounts ranging between about 5.0 mg/l and about 250 mg/l, and preferably about 50 mg/l of working fermentation volume.

The resin is added at about 1–15 g/l of fermentation volume, preferably at 3 g/l. Higher concentrations do not result in higher sporulation, but lower concentrations result in substantially lower sporulation with certain strains. The optimum resin amount is strain-dependent in that some strains exhibit higher sporulation at the higher end of the above range. Strains that grow vigorously do not need resin.

The preferred conditions for sporulation are generally the same as those for vegetative growth, except that the pH is preferably about $6.8\pm 0.1$ (a higher pH of up to about $8.1\pm 0.1$ may be tolerated but is not necessary.) Control of pH is important and can be achieved by addition of HCl or a sodium-free base, as necessary.

By the present invention, sporulation rates of 80 to more than 95% are achieved. The sporulation rate given is based on the vegetative cell density at the end of the growth phase.

If desired, the resin may be removed by filtration before harvesting the spores.

The spores may be harvested by addition of talc ($MgSIO_4$) or hydrous aluminum silicate and centrifugation. Talc (about 0–10 g/l; preferably 5 g/l of 400 mesh) is used to help separate the spores from the culture medium. Separation is preferably conducted by high-speed centrifugation. The major pellet components are talc, resin (if used and not previously removed) spores, and $CaCO_3$. The pellet is preferably resuspended in distilled water containing 0.1% trehalose (10 g/ml) and then freeze-dried. The amounts given in this and the following paragraph pertain to commercial scale production.

The dry weight yield of this primary fermentation product is about 7.7–12.5 g/l of sporulation medium.

The primary fermentation product should not be hygroscopic; removal of unused and spent media by centrifugation helps accomplish this. Alternatively, the spores may be concentrated by filtration, without addition of talc, $CaCO_3$ etc., washed several times with water (to clean them of spent medium) and then freeze- or spray-dried. If talc and $CaCO_3$ are not used, spore counts per gram of primary fermentation products should be higher.

The preferred composition of the talc-centrifuged, freeze-dried primary fermentation product of a commercial-scale embodiment of the present invention is as follows:
mature spores—about 15–21%;
$CaCO_3$ (400 mesh)—about 10–14%;
resin—about 28–0%;
talc—about 47–65%;
trehalose—about 0.9–1.4%
A preferred spore density is about $0.9-1.5 \times 10^{11}$ spores/gram gram of freeze-dried product containing talc and resin.

As stated previously, essentially all of the milky disease spores produced in vitro in liquid media as discussed above have no sporangium on harvesting. Because these spores are infective especially when administered per os, they are milky disease spores. Accordingly, in view of the present invention, the growth and sporulation pattern of milky disease bacilli as exemplified by B. popilliae is as depicted in FIG. 1.

Figure 1:
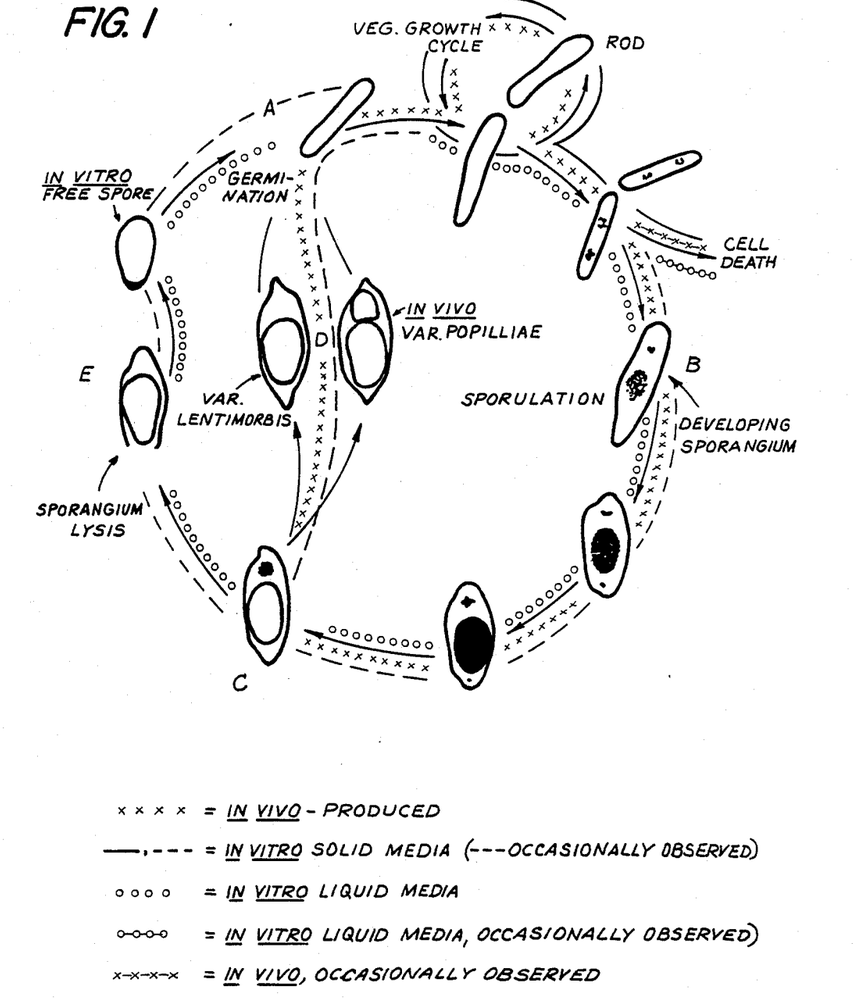
FIG. 1 is a schematic diagram of the growth and sporulation patterns of *B. popilliae* in vivo and in liquid and solid media in vitro.

FIG. 1 describes the different growth and sporulation patterns of B. popilliae depending on the environment in which the organism is grown. The in vivo pattern ABCDA is shown by the line of crosses. The in vitro pattern ABCDA and ABCEA in solid media is shown by the solid line and by the broken line, where appropriate, to signify occasional observation. (Sporulation is difficult to achieve in solid media.)

Finally, the in vitro pattern in liquid media ABCEA is shown by the line of open circles.

Bacterial rods result from spore germination at point A in the cycle and undergo a vegetative growth cycle. Upon imposition of an adverse environmental condition, the rods will either die or sporulate. The beginning of sporulation, B, is marked by development of a sporangium in vivo and in vitro in both solid and liquid media. Progressively, endospore and parasporal body formation will become apparent. In vivo and in solid media the spore will become apparent. In vivo and in solid media the spore will mature at D into either a B. popilliae-type spore containing a parasporal body or a B. lentimorbus-type spore not containing a refractile parasporal body. In liquid media, the sporangium will eventually lyse at E (at the time of spore maturation) and no refractile parasporal body will be observed except rarely. Occasionally, this type of growth development will also be observed in solid media.

The spore maturation pathway C-E-A was not associated with B. popilliae prior to the present invention, or even if it had been, it would not have been associated with milky disease spore that would be infective when administered per os. Hence, prior to the present invention, sporangiumfree spores would not be considered (by those skilled in the art) capable of forming the basis for an insecticidal composition for application in fields, gardens, orchards, pastures, lawns, and containers (sometimes collectively referred to as "the field").

However, the infectivity of the naked spores of the present invention has been confirmed. In fact, the naked spores of the present invention have been found to be most infective (relative to the in vivo-produced, sporangium bearing spores) when administered per os rather than by injection.

Figure 2:
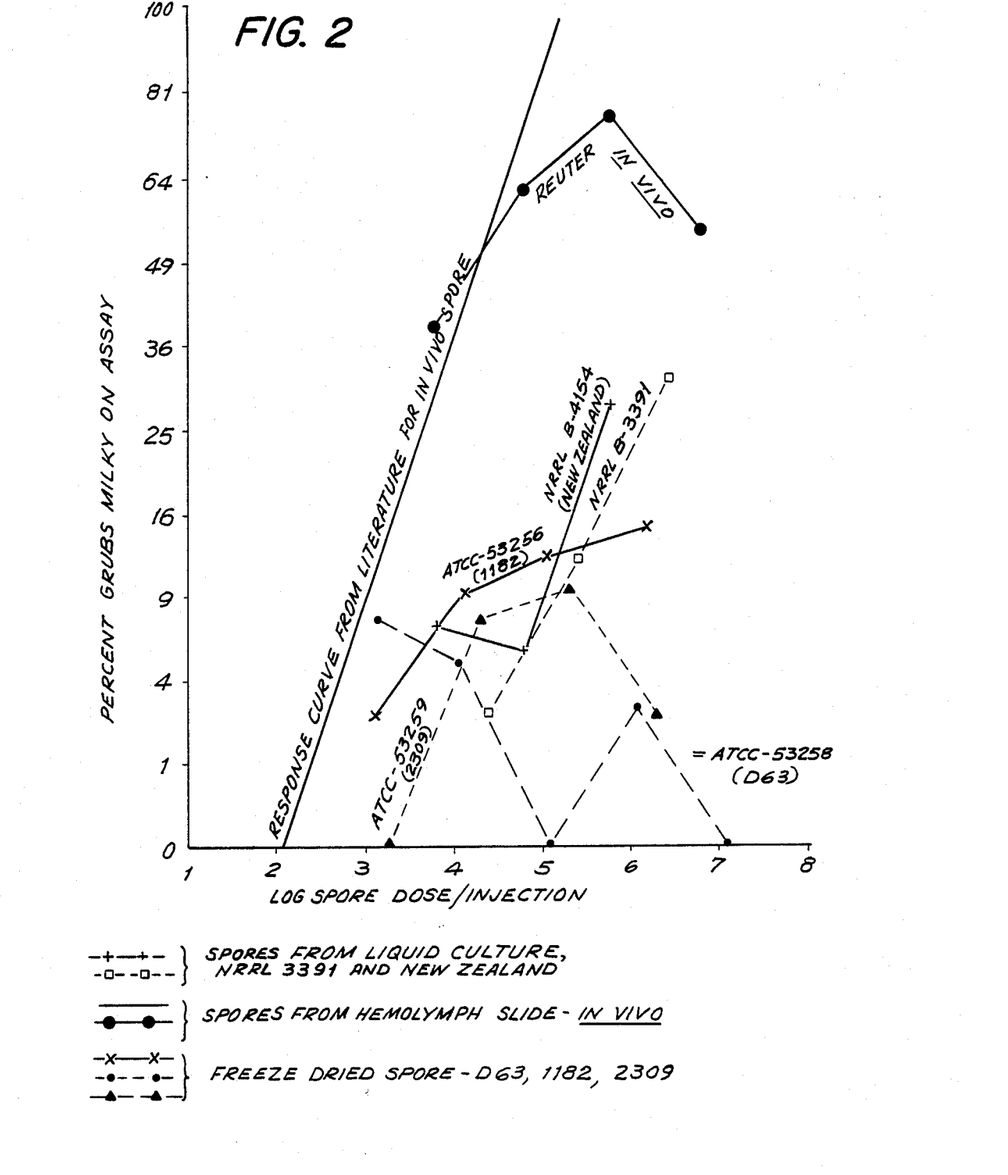
FIG. 2 is a plot of the square root of the percent infectivity of *B. popilliae* spore against the log of the spore dose administered per injection in an injection bioassay.

With particular reference to FIG. 2, the results of injection assays reported in the literature were compared with those obtained with in vivo-produced (sporangium-bearing) spore, and a variety of in vitro-produced spores. When the square root of the percentage of the Japanese beetle grubs that tested milky on assay is plotted against the log spore dose per injection, the literature reports a straight line response with a threshold of $10^2$ spores progressively increasing to 100 percent milkiness at a dose of about $10^5$.

The particular in vivo tests conducted as positive controls in the experiments reported here (marked by dark circles) were within the range of infectivity reported in the literature for doses up to about $10^5$ spores/injection. At higher doses, however, the rate of additional infection declined as a function of the additional spore dose and eventually infectivity decreased substantially. This indicates that there is a maximum threshold dose after which infectivity-by-injection declines.

When the in vitro-produced spores of the present invention were tested for infectivity by injection, the infectivity was invariably lower than that reported in the literature for in vivo spores at the same dose and was substantially lower than that of the positive control test. At any given dose, the in vivo spore infectivity was several times higher and at higher doses the difference in infectivity increased manifold instead of being reduced. Moreover, the spores from liquid culture (marked by x for the NRRL B-4154 variety and open squares for the NRRL B-3391 variety) were generally more infective than the freeze-dried spores of other varieties at comparable doses.

It is evident from the above results, that if the injection assay had been the only infectivity test conducted, the results would be considered disheartening. The results indicate that, in most cases, each grub would have to be infected with tens of thousands to millions of spores in order to develop any substantial percentage of disease injection. This low infectivity could be easily masked by background levels. From these results, one of ordinary skill in the art would conclude that the in vitro-produced spores in accordance with the present invention would not have substantial utility in insecticidal of compositions for use in the field. Accordingly, if the present inventors had continued to accept the widely-held view that the injection bioassay provides higher infectivity at a given dose than a per os bioassay, they would have abandoned further efforts to use in vitro-produced spore in insecticidal compositions.

Figure 3:
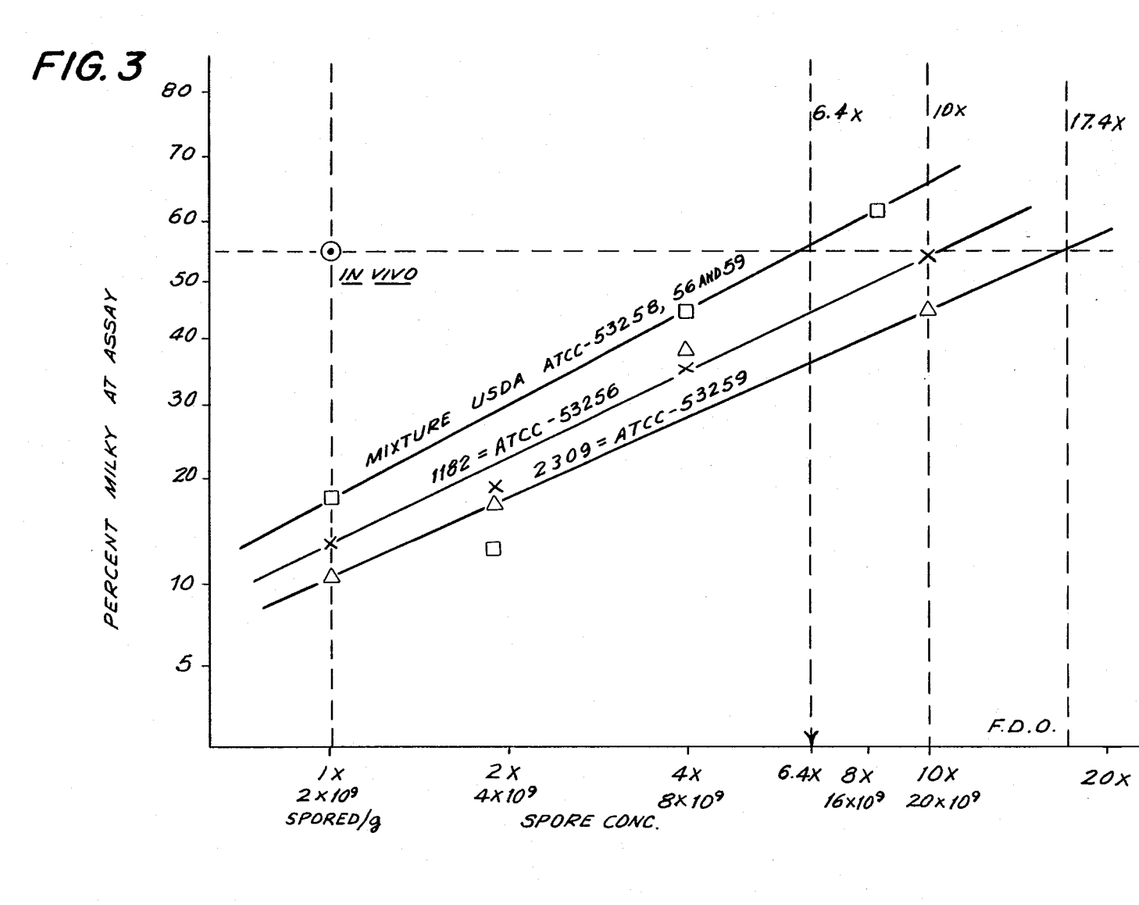
FIG. 3 is a plot of the percent infectivity of *B. popilliae* spore on a probability scale against the log of the spore concentration in a soil inoculation bioassay.

With particular reference to FIG. 3 and Table II, the results of a soil inoculation bioassay are described below.

These results show that in a soil inoculation bioassay wherein in vitro spore was introduced in a container of soil together with Japanese beetle third instar larvae the in vitro produced spore showed lower infectivity than the in vivo spore at the same concentration. Unlike the injection assays, however, at higher spore concentrations, the infectivity continued to increase and reached the levels of in vivo spore infectivity at concentrations anywhere from about 6 to about 18 times the in vivo spore concentration.

Moreover, a mixture of in vivo USDA-std material, ATCC-53256 and ATCC-53259 (Formulation Z) proved to be substantially more infective than mixtures of in vivo USDA std and either ATCC-53256 or ATCC-53259 with comparable proportions of in vivo material. Formulation Z has infectivity comparable to that of the in vivo product at 6.4 times the concentration of the in vivo material (USDA-std) shown in FIG. 3. A formulation containing 0.006% of the USDA standard (in vivo spore), 3.906% of ATCC-53258, 48.044% of ATCC-53256, and 48.044% of ATCC-53259 corresponds to this concentration and is particularly preferred. This spore content translates into approximately $3 \times 10^{11}$ spores/lb of the formulation.

The lines shown in FIG. 3 correspond approximately to the best fit through the data points (except for the material containing ATCC-53256 at $4 \times 10^9$ spores/gram).

An important characteristic of the present formulations is that they contain very small amounts of in vivo-produced spore. Although higher proportions of in vivo-produced spore are possible, they are unnecessary and uneconomical. Thus, although in principal the only requirement for the formulation of the present invention is that they contain a quantity of in vitro-produced spore such that it substantially contributes to the infectivity of the formulation, in practice, it is preferred to use formulation containing minimum amounts of in vivo-produced spore such that (when combined with the in vitro produced spore) will result in economically produced formulations having acceptable infectivity.

Of course, it will be understood that inasmuch as the infectivity of spores is strain-dependent, the above ranges serve as guidelines only and cannot be generalized for every strain of in vitro or in vivo produced spore. In every instance where in vivo and in vitro-produced spore is used in combination, however, the composition contains sufficient in vitro-produced spore to have a substantial (increasing) effect in the infectivity of the composition as a whole.

The final insecticidal compositions according to the present invention also preferably include a carrier or diluent. Solid compositions in powder, granular, pellet or bait form are preferred. Solid carriers include but are not limited to talc, calcium carbonate, hydrous aluminum silicate, kaolin, corn cob, vermiculite and mixtures thereof. Hydrous aluminum silicate (for powder formulations) and corn cob (for granular formulations) are particularly preferred. Preferably the carrier or filler comprises from about 98.5% to over 99.9% by volume of the composition, when the active ingredient is in the form of a primary fermentation product, such as the product of Example 1, below.

Liquid compositions generally comprise the same amounts of active ingredient suspended in a liquid diluent, such as a mixture of mineral oil and water (preferably at a 1:9 ratio).

Liquid sprayable compositions will also contain a wetting agent (e.g., 0.5–1.0% wetanol from Glycol Chemicals, Inc., New York, N.Y.), an emulsifying agent (e.g., 0.1–0.5% Tween 80 polysorbate from ICI Americas, Wilmington, DE) and dispersing agent (e.g., 2"4% Blancol from GAF, Chattanuga, Tenn., or 3% Lomar—TW from Hopco Chemical Co., Newark, N.J.). The active ingredient will be used in the form of a wetable powder containing the equivalent of 7–12 grams of primary fermentation product/lb of dry weight and also containing as much additional filler (such as talc, or hydrous aluminum silicate, etc.) as a bodying agent to improve the suspendability of the solid constituents.

The invention is further described below by particular examples that are intended to illustrate the present invention without limiting its scope.

EXAMPLE 1

Method of Producing Milky Disease Spore In Vitro

Viable seed cultures of NRRL-B 2309 strain *B. popilliae* were provided on agar plates. The cell line was maintained in J medium containing 1% tryptone (Difco), 0.5% yeast extract (Difco), 0.3% $K_2HPO_4$, 0.2% trehalose and 1.5% agar (Difco) in distilled water. The medium prior to addition of trehalose was autoclaved at 120° C./15 psi for 15–20 minutes. The sugar was autoclaved separately and then added to the other autoclaved ingredients. Poured plates or slants were inoculated from the B 2309 culture and incubated at 25° C. The cells were transferred at least weekly to new medium.

From the maintenance cultures, submerged cultures were prepared. First, a liquid medium was prepared containing 1.0% soluble starch; 0.1% trehalose (Kodak); 0.5% yeast extract (Difco); 0.3% $K_2]1$ $HPO_4$; 0.1% $CaCO_3$ (400 mesh); and distilled water (starting pH 7.6). The medium was autoclaved separately psi for 15-°minutes. Trehalos e was autoclaved separately from the other components. It was not necessary to adjust the pH by addition of HCl.

A 1-liter shaker flask containing 300 ml of the above liquid medium was aseptically inolculated with seed culture from the maintenance culture, then incubated on a shaker table at 32°±1° C. at approximately 250 rpm for 14 hours.

When microscopic counts reached approximately $1 \times 10^9$ rods per ml, 3.3% inoculum was added to 10 liters of the above medium. Incubation took place at 32° C. with mechanical mixing at 250 rpm and sterile aeration at 0.2 volumes of air per volume of medium per minute (vvm). After 4 hours of culture, 30 ml of 5% HODAG HD-62 antifoam (autoclaved at 120° C./15 psi for 15–20 min) was added aseptically. The pH was not regulated by addition of KOH or HCl and fell from 7.6 at the beginning of incubation to 6.25 at the end of the log growth phase.

The growth curve was monitored microscopically. When cell numbers reached $1.2 \times 10^9$ rods/ml (at about 18 hours post-inoculation) the pH was raised to 6.8 by sterile addition of KOH and the sporulation adjuvants were added.

The sporulation adjuvants were sterilized separately by autoclaving at 121° C. (15 psi) for 15–20 minutes and added aseptically to the fermenter at the following rates:

1. $MnSO_4$ in solution at 50 mg/per ml of distilled water; added at rate of 1 ml/l of fermenter working volume.
2. Adsorbent resin (amberlite XAD-7), thoroughly washed with methanol and distilled water, was added before autoclaving at a rate of 3 grams (dry resin weight) per liter of fermenter working volume to a final amount of 30 g of resin in 300 ml water.

The sporulation phase conditions are: temperature—32°±1° C.; mechanical mixing—250 rpm; sparging with sterile air at 0.5 vvm, pressure at 0.5 psig. pH was not adjusted following addition of adjuvants and rose slowly throughout the sporulation phase to a final value of 8.0. A pH as high as 8.2 is permissible but unnecessary as it is not accompanied by maximization of sporulation. The sporulation period was completed in about 20 hours from the addition of sporulation adjuvants. Completion of sporulation (95%) was microscopically determined.

Harvesting of the spores after removal of the resin by filtration took place by continuous pass, high-speed centrifugation for removal of all soluble components of the spent medium and production of a nonhygroscopic primary fermentation product. Hydrous aluminum silicate was added to the culture volume at 5 grams/liter, 400 mesh, prior to centrifugation. This material assisted the separation of the B 2309 spores together with undissolved calcium carbonate and resin from the supernatant. Centrifugation took place in a Sharples table model centrifuge Model No. T1-P (manufactured by Penwalt Corp.).

The pelleted paste, i.e. the spore—talc—solid component mixture, was resuspended in 0.1% trehalose and distilled water (10 ml/gram of pellet) and the suspension was freeze-dried. The paste weighed 81.4 grams and the dry weight yield of the spore mixture was 48.8 grams. The actual spore yield from 10.6 liters of culture/sporulation medium was 1.21 x $10^{13}$ spores. This corresponds to a spore content of 95% based on the number of cells at the end of the growth phase. The thus prepared primary fermentation product is aged, as the germinabiltiy of freshly made spores is substantially lower than that of aged spores, and it is compounded into a composition suitable for application in the field.

EXAMPLE 2

Method for Producing Milky Disease Spore In Vitro

The procedure of Example 1 was used but no resin was added as a sporulation agent. Use of resin has been found to improve the sporulation rate in certain strains, such as ATCC-53258 and ATCC-53259, but did not have a noticeable effect on the sporulation rate of ATCC-53256.

EXAMPLE 3

Injection Bioassay

The injection bioassays were conducted in accordance with the procedure of Dutky, et al described in U.S. Pat. No. 2,293,890, incorporated by reference herein.

Except where indicated otherwise in Table I, below, 40 grubs per test were injected with either a sample of settled spores from a refrigerated liquid culture, or a sample obtained from hemolymph slides for the in vivo material, or reconstituted freeze-dried spore preparations in distilled water. The injection volume was 0.003 ml per injection and only one injection was administered to each grub. The dose in spores per injection and the *B.popilliae* strains used are given in Table I, below.

After injection, the grubs were monitored twice a week to look for milky symptoms. Grubs displaying the milky symptoms were assayed by microscopic observation and so were any dead grubs. At the end of seven weeks, any remaining grubs were sacrificed and also assayed.

The results are shown in Table I, below.

TABLE I

| Spore Provenance | Dose (Spores/Grub) | Results No. Milky/Total Assayed | % Infectivity |
|---|---|---|---|
| in vivo | $6.62 \times 10^6$ | 22/39[a] | 56.41 |
| (hemolymph slide) | $6.62 \times 10^5$ | 32/40 | 80.00 |
| spore | $6.62 \times 10^4$ | 26/40 | 65.00 |
| | $6.62 \times 10^3$ | 13/14 | 32.50 |
| in vitro | $1.02 \times 10^6$ | 6/39[b] | 15.30 |
| ATCC-53256 | $1.02 \times 10^5$ | 5/40 | 12.50 |
| | $1.02 \times 10^4$ | 4/40 | 10.00 |
| | $1.02 \times 10^3$ | 1/40 | 2.50 |
| in vitro | $1.36 \times 10^6$ | 1/40 | 2.50 |
| ATCC-53259 | $1.36 \times 10^5$ | 4/40 | 10.00 |
| | $1.36 \times 10^4$ | 3/39[b] | 7.50 |
| | $1.36 \times 10^3$ | 0/30 | 0.00 |
| in vitro | $9.10 \times 10^6$ | 0/40 | 0.00 |
| ATCC-53258 | $9.10 \times 10^5$ | 1/40 | 2.50 |
| | $9.10 \times 10^4$ | 0/39 | 0.00 |
| | $9.10 \times 10^3$ | 2/40 | 5.00 |
| | $9.10 \times 10^2$ | 3/40 | 7.50 |
| in vitro | $1.91 \times 10^6$ | 0/40 | 0.00 |
| NRRL B-2519 | $1.91 \times 10^5$ | 0/40 | 0.00 |
| | $1.91 \times 10^4$ | 0/40 | 0.00 |
| in vitro | $2.51 \times 10^6$ | 13/40 | 32.50 |
| NRRL B-3391 | $2.51 \times 10^5$ | 5/40 | 12.50 |
| | $2.5 \times 10^4$ | 1/39[b] | 2.56 |
| in vitro | $6.29 \times 10^5$ | 5/18[a] | 27.78 |
| NRRL B-4154 | $6.29 \times 10^4$ | 1/18[a] | 5.56 |
| | $6.29 \times 10^3$ | 2/29[a] | 7.00 |
| $H_2O$-injection | 0 | 0/20 | 0.00 |
| | 0 | 0/20 | 0.00 |
| No-injection | 0 | 0/40 | 0.00 |
| | 0 | 1/20 | 5.00 |

[a] 1 missing
[b] 1 adult
[c] pupa

EXAMPLE 4

Soil Inoculation Bioassay

Soil inoculation bioassays were performed in accordance with the method developed by Dutky and described in Schwartz, P. H. et al 1970 *J. Invert. Pathol.* 15:, 126–128 (incorporated by reference), as follows: First concentrates of spore were prepared by mixing the spores with calcium carbonate and with soil containing roots of sprouted redtop. The soil samples were placed on plastic trays, each containing to tablespoons of soil. The soil was moistened with formaldehyde (40% USP solution) and diluted 1:1000 with water. One larva was added to each tray.

The soil was moistened and the sprouted redtop was replaced as necessary throughout the tests. The results are shown in Table II, below.

TABLE II

| spore provenance | inoculation rate/kg soil | results No. Milky/Total Assayed | infectivity (%) |
|---|---|---|---|
| USDA-std | $2.0 \times 10^9$ | 18/28[a] | 64.29 |
| (in vivo) | $0.5 \times 10^9$ | 21/34[a] | 61.76 |
| $1 \times 10^8$ spores/g | $2.0 \times 10^9$ | 12/26[a] | 46.15 |
| | $2.0 \times 10^9$ | 21/26[a] | 00.77 |
| | $0.5 \times 10^9$ | 19/31[a] | 61.29 |
| | $0.1 \times 10^9$ | 10/28[a,b] | 35.71 |
| | $2.0 \times 10^9$ | 17/31[a] | 54.84 |
| in vivo spike | $2.0 \times 10^9$ | 23/25[a] | 92.00 |
| ATCC-53258 | $2.0 \times 10^{12}$ | 19/40 | 47.50 |
| raw concentrate | $2.0 \times 10^{10}$ | 8/27[a] | 29.63 |
| | $2.0 \times 10^9$ | 2/10[a] | 20.00 |
| ATCC-53258 | $2.0 \times 10^{12}$ | 25/32[a] | 81.25 |
| concentrate | $2.0 \times 10^{10}$ | 15/30[a] | 50.00 |
| | $2.0 \times 10^9$ | 2/35[a] | 5.71 |
| Formulation A | $2.0 \times 10^{10}$ | 10/26[a] | 38.46 |
| | $2.0 \times 10^9$ | 5/23[a] | 21.74 |

TABLE II-continued

| spore provenance | inoculation rate/kg soil | results No. Milky/ Total Assayed | infectivity (%) |
|---|---|---|---|
| | $2.0 \times 10^{10}$ | 12/29[a] | 41.38 |
| | $2.0 \times 10^{9}$ | 6/32[a] | 18.75 |
| Formulation B | $2.0 \times 10^{10}$ | 27/34[a] | 79.40 |
| | $2.0 \times 10^{9}$ | 13/31[a] | 41.90 |
| Formulation C | $2.0 \times 10^{10}$ | 20/27[a] | 74.07 |
| | $2.0 \times 10^{9}$ | 12/25[a] | 48.00 |
| Formulation D | $2.0 \times 10^{10}$ | 19/28[a] | 67.86 |
| | $2.0 \times 10^{9}$ | 9/23[a] | 39.13 |
| ATCC-53256 | $2.0 \times 10^{12}$ | 10/36[a] | 27.78 |
| | $2.0 \times 10^{10}$ | 20/37[a] | 54.05 |
| | $2.0 \times 10^{9}$ | 4/35[a] | 11.43 |
| ATCC-53259 | $2.0 \times 10^{10}$ | 14/31[a] | 45.16 |
| | $2.0 \times 10^{9}$ | 7/35[a] | 20.00 |
| | $2.0 \times 10^{8}$ | 2/39[a] | 5.26 |
| control | 0.0 | 0/25[a] | 00.00 |
| | 0.0 | 0/19[c] | 00.00 |
| | 0.0 | 0/20 | 00.00 |
| | 0.0 | 0/31[a] | 00.00 |
| Formulation $X_1$ | $2.0 \times 10^{9}$ | 4/30[a] | 13.33 |
| Formulation $X_2$ | $4.0 \times 10^{9}$ | 7/36[a] | 19.44 |
| Formulation $X_3$ | $8.0 \times 10^{9}$ | 13/34[a] | 38.24 |
| Formulation $Y_1$ | $2.0 \times 10^{9}$ | 3/29[a] | 10.34 |
| Formulation $Y_2$ | $4.0 \times 10^{9}$ | 5/29[a] | 17.24 |
| Formulation $Y_3$ | $8.0 \times 10^{9}$ | 14/35[a] | 40.00 |
| Formulation $Z_1$ | $2.0 \times 10^{9}$ | 5/28[a] | 17.86 |
| Formulation $Z_2$ | $4.0 \times 10^{9}$ | 5/39[a] | 12.82 |
| Formulation $Z_3$ | $8.0 \times 10^{9}$ | 15/34[a] | 44.12 |
| Formulation $Z_4$ | $16.0 \times 10^{9}$ | 24/39[a] | 61.54 |

[a]Remainder of 40 decomposed
[b]1 adult
[c]Remainder of 20 decomposed

The USDA standard was used for inoculation at a concentration of $1 \times 10^8$ spores per gram.

"In vivo spike" was in vivo material obtained from a freeze-dried mixture of infected grubs and calcium carbonate containing $2.4 \times 10^4$ spores per gram.

ATCC-53258 raw concentrate was a freeze-dried primary fermentation product prepared in accordance with the present invention and containing $0.825 \times 10^{11}$ spores/gram.

ATCC-53258 concentrate was a mixture of ATCC raw concentrate (99.96% by weight) and in vivo spike (0.04%) by weight.

Formulation A consisted of ATCC-53258 concentrate diluted with hydrous aluminum silicate to a count of $1 \times 10^8$ spores per gram.

Formulation B was the same as Formulation A except that it contained 99.2% by weight of ATCC-53258 raw concentrate and 0.8% of in vivo spike. This formulation was in turn diluted with hydrous aluminum silicate to a count of $1 \times 10^8$ spores per gram.

Formulation C was the same as Formulation B except that it contained 99.6% of ATCC-53258 raw concentrate and 0.4% in vivo spike. This was diluted with hydrous aluminum silicate to a count of $1 \times 10^8$ spores per gram.

Formulation D was the same as Formulation C except that it contained 99.8% of ATCC-53258 raw concentrate and 0.2% in vivo spike diluted with hydrous aluminum silicate to a count of $1 \times 10^8$ spores per gram.

ATCC-53256 was freeze-dried primary fermentation product produced in accordance with the present invention and containing $1.34 \times 10^{11}$ spores per gram.

ATCC-53259 was freeze-dried primary fermentation product produced in accordance with the present invention and containing $1.53 \times 10^{11}$ spores per gram.

Formulations X, Y and Z contained various amounts of USDA standard, ATCC-53258 raw concentrate, and either or both of ATCC-53256 and ATCC-53259 in the following proportions:

| | Percent Spore Product (By Weight) | | | |
|---|---|---|---|---|
| | USDA-std | ATCC-53258 Raw Conc. | ATCC-53256 | ATCC-53259 |
| Formulation X | | | | |
| $X_1$ | 0.032 | 19.944 | 79.974 | — |
| $X_2$ | 0.018 | 11.109 | 88.873 | — |
| $X_3$ | 0.009 | 5.882 | 94.109 | — |
| Formulation Y | | | | |
| $Y_1$ | 0.032 | 19.994 | — | 79.974 |
| $Y_2$ | 0.018 | 11.109 | — | 88.873 |
| $Y_3$ | 0.009 | 5.882 | — | 94.109 |
| Formulation Z | | | | |
| $Z_1$ | 0.032 | 19.994 | 39.987 | 39.987 |
| $Z_2$ | 0.018 | 11.108 | 44.437 | 44.437 |
| $Z_3$ | 0.008 | 5.882 | 47.055 | 47.055 |
| $Z_4$ | 0.005 | 3.030 | 48.482 | 48.482 |

Although the present invention has been described above by reference to a preferred embodiment, those of ordinary skill in the art will readily appreciate that many additions, deletions, or modifications are possible all within the scope of the present invention and the following claims.

What is claimed is:

1. An insecticidal composition for use in controlling Scarabaeide by application to fields, orchards, pastures, lawns, gardens or containers comprising as an active ingredient an insecticidally effective amount of sporangium-free spore produced in culture in sporangium-free form and selected from the group consisting of spores of a pathogen of a species of the genus Bacillus causing milky disease in said Scarabaeide and mixtures of spores from at least two types, strains, isolates or species of said Bacillus; and a carrier or diluent.

2. The composition of claim 1, wherein said spore is selected from the spore Bacillus popilliae group of milky disease bacilli.

3. The composition of claim 1 wherein said carrier is selected from the group consisting of talc, calcium carbonate, hydrous aluminum silicate, kaolin, corn cob, vermiculite and mixtures thereof.

4. The composition of claim 1 wherein said spore is a mixture of spores of at least two strains of the same species of said Bacillus.

5. The composition of claim 1 also comprising conventional, in-vivo produced, sporangium-bearing spore wherein said sporangium-free spore is responsible for a measurable portion of the total per os infectivity of said composition as measured by soil inoculation bioassay.

6. The composition of claim 1, comprising from about 6 to about 18 times the number of spores contained in a comparison insecticidal composition wherein the active ingredient is solely in-vivo-produced sporangium-bearing spore of the same species as that from which the in-vitro-produced spores was derived.

7. The composition of claim 1 comprising from less than 100% to about 99.99% sporangium-free spore and from more than 0% to about 0.01% sporangium-bearing spore, said percentages being based on the total number of spores in said composition.

8. The composition of claim 1 wherein said amount is sufficient to confer to said composition infectivity of at least 50% as measured by soil inoculation bioassay in which the soil is inoculated at the rate of 20 grams of said composition per kilogram of treated soil.

9. The composition of claim 5 wherein said amount of said in-vivo-produced spore contained in said composition is at most 0.07% of the amount of spore contained in a comparison insecticidal composition having the same infectivity as measured by soil inoculation bioassay but containing solely sporangium-bearing, in-vivo-produced spore.

10. The composition of claim 4 wherein said pathogen is Bacillus popilliae and said spore is a mixture of 11. The composition of claim 10 also comprising about 0.006% of sporangium-bearing spore, and about 3.9% of in-vitro-produced, sporangium-free spore from strain ATCC-53258 based on the total spore content of the composition, the balance being a 50/50 mixture of sporangium-free spores from ATCC-53259 and ATCC-53256.

12. A method for producing milky disease Bacillus spore in vitro comprising:
  under aerobic conditions at a controlled pH, culturing vegetative cells of said Bacillus in a liquid medium said medium comprising:
    from about 0.1 to about 2.0% soluble starch;
    from about 0.1 to about 0.2% trehalose;
    from about 0.5 to about 1.5% yeast extract;
    from about 0.1 to about 0.6% $K_2HPO_4$; and
    from about 0.0 to about 0.3% $CaCO_3$; and
  adding, as a sporulation adjuvant from about 5 to about 250 mg/l of manganese sulfate at the end of the vegetative growth stage, and incubating said culture until sporulation occurs, said sporulation resulting in sporangium-free spore.

13. The method of claim 12 further comprising adding as an additional sporulation adjuvant a resin selected from the group consisting of nonionic adsorbent resins, cationic exchange resins and anionic exchange resins, all of said resins being made from copolymers of styrene and divinylbenzene, or acrylic esters in amounts ranging between 1 and about 15 g/l.

14. The method of claim 13 wherein said Bacillus is Bacillus popilliae and said liquid medium comprises 1.0% soluble starch; 0.1% trehalose; 0.5% yeast extract; 0.3% $K_2HPO_4$; and 0.2% $CaCO_3$ by weight; and said sporulation adjuvant comprises 50 mg/l $MnSO_4$.

15. The method of claim 13 wherein said additional sporulation adjuvant comprises 3 g/l of a nonionic absorbent resin made from a copolymer of acrylic esters cross-linked with trimethylacrylate functional groups.

16. The method of claim 12 comprising incubating said culture until at least 80% sporulation occurs based on the vegetative cell density at the end of the growth phase.

17. An in vitro process for producing Bacillus popilliae spores, said processing comprising:
  providing seed cultures of said Bacillus;
  forming an inoculum from said cultures by aseptically transferring vegetative cells of said Bacillus to a liquid culture medium;
  Aseptically inoculating with said inoculum a previously sterilized medium comprising about 0.1–2.0% soluble starch; about 0.1–0.6% $K_2HPO_4$; about 0.0–0.3% $CaCO_3$; and distilled water and having a pH between about 6.8 and about 8.1;
  fermenting said inoculated medium in a fermenter at about $32° \pm 1°$ C., 0.5 psig at a pH between about 7.2 and about 7.4, under mechanical mixing and sterile air supply at about 0.2–0.5 vvm until the cell density of said vegetative cells reaches about $1 \times 10^9$ rods/ml;
  aseptically adding a sterilized sporulation adjuvant to said vegetative cell fermented culture, said adjuvant comprising at least one of: $MnSO_4$ solution in distilled water to a final concentration of about 0.5–250 mg/l and an adsorbent resin, in an amount of 1–15 g/l on a dry weight bases; and
  incubating said culture at about $32° \pm 1°$ C., 0.5 psig, under mechanical mixing, in the presence of sterile aeration at about 0.5 vvm and at a pH about equal to or higher than 6.8 or a time sufficient for sporulation to be completed, whereby at least 85% of the cells present in said culture sporulate and yield sporangium-free spore.

18. The method of claim 17, wherein said resin is selected from the group consisting of nonionic adsorbent resins and cationic exchange and anionic exchange resins made from copolymers of styrene and divinylbenzene or acrylic esters.

19. The method of claim 17, wherein said medium comprises: 1.0% soluble starch; 0.1% trehalose; 0.5% yeast extract; 0.3% $K_2HPO_4$ by weight; and 0.2% $CaCO_3$; and said sporulation adjuvant comprises at least one of 50 mg/l $MnSO_4$ and 3 g/l of an absorbent resin made from a copolymer of acrylic esters cross-linked with trimethylacrylate functional groups.

* * * * *

UNITED STATES PATENT AND TRADEMARK OFFICE
CERTIFICATE OF CORRECTION

PATENT NO. : 4,824,671             Page 1 of 5

DATED : April 25, 1989

INVENTOR(S) : Beth-Jayne Ellis; Frederick Obenchain; Raj Mehta

It is certified that error appears in the above-identified patent and that said Letters Patent is hereby corrected as shown below:

On the title page, item [57]:
In the Abstract, line 6: "trechalose" should read --trehalose--.

Col. 1, line 40: "effective" should read --infective--.

Line 57: "larvae" should read --larval--.

Col. 2, line 33: "rase" should read --rose--.

Line 47: "thud" should read --thus--.

Col. 3, line 5: "triptose" should read --tryptose--.

Line 48: "do" should read --does--.

Line 60: "doe" should read --do--.

Col. 4, line 34: "noninfective" should read --infective--.

Line 39: "is" should read --if--.

Line 41: "ad- ministered" should read --administered--.

Col. 5, line 37: "giumfree" should read --gium-free--.

Line 44: "rangiumfree" should read --rangium-free--.

Col. 6, line 23: "(RLI-D-1182-W)" should read --(RLI-1182-W)--.

UNITED STATES PATENT AND TRADEMARK OFFICE
CERTIFICATE OF CORRECTION

PATENT NO. : 4,824,671

DATED : April 25, 1989

INVENTOR(S) : Beth-Jayne Ellis; Frederick Obenchain; Raj Mehta

It is certified that error appears in the above-identified patent and that said Letters Patent is hereby corrected as shown below:

Line 26: delete "," after "spores"; insert --formed-- after "are".

Line 34: "does" should read --dose--.

Line 42: delete "in", insert --of--.

Line 53: after "yeast" and before ",", insert --extract--.

Col. 7, line 34: "sporulationtoxic" should read --sporulation-toxic--.

Line 40: "1.5'10$^9$" should read --1.5x10$^9$--.

Col. 8, line 30: "styrenedivinylbenzene" should read --styrene-divinylbenzene--.

Line 33: "styrene/divinylbenzene" should read --styrene-divinylbenzene--.

Line 62: "(MgSIO$_4$)" should read --(MgSiO$_4$)--.

Col. 9, line 26: delete second "gram".

UNITED STATES PATENT AND TRADEMARK OFFICE
CERTIFICATE OF CORRECTION

PATENT NO. : 4,824,671

DATED : April 25, 1989

INVENTOR(S) : Beth-Jayne Ellis; Frederick Obenchain; Raj Mehta

It is certified that error appears in the above-identified patent and that said Letters Patent is hereby corrected as shown below:

Line 68: "sporangiumfree" should read --sporangium-free--.

Col. 10, line 54: delete "of".

Col. 11, line 32: insert --a-- after "use".

Line 34: before "will" insert --it--.

Line 66: "ocas," should read --cas,--.

Line 67: "2"4% should read --2-4%--.

Col. 12, line 2: "wetable" should read --wettable--.

Line 29: change "K2]1 HPO4" to --$K_2HPO_4$--.

Line 31: delete "separately psi for 15-°minutes", insert --at 121°C/15 psi for 15-20 minutes--.

Line 32: change "Trehalos e" to --Trehalose--.

Col. 13, line 34: change "germinabiltiy" to --germinability--.

Col. 14, Table II, col. 4, change "00.77" to --80.77--.

Col. 16, line 34: "Bacillus" should read --<u>Bacillus</u>--.

UNITED STATES PATENT AND TRADEMARK OFFICE
CERTIFICATE OF CORRECTION

PATENT NO. : 4,824,671

DATED : April 25, 1989

INVENTOR(S) : Beth-Jayne Ellis; Frederick Obenchain; Raj Mehta

It is certified that error appears in the above-identified patent and that said Letters Patent is hereby corrected as shown below:

Line 39: delete "spore"; change "Bacillus popilliae" to --<u>Bacillus popilliae</u>--.

Line 47: change "Bacillus" to --<u>Bacillus</u>--.

Col. 17, line 9: change "Bacillus popilliae" to --<u>Bacillus popilliae</u>--; after "of" insert --sporangium-free spores of strains ATCC-53529 and ATCC-53526--.

Line 37: delete "on", insert --or--.

Line 39: change "Bacillus" to --<u>Bacillus</u>--.

Line 40: change "Bacillus popilliae" to --<u>Bacillus popilliae</u>--.

Col. 18, line 5, delete "Bacillus popilliae", insert --<u>Bacillus popilliae</u>--.

Line 7: delete "Bacillus", insert --<u>Bacillus</u>--.

UNITED STATES PATENT AND TRADEMARK OFFICE
CERTIFICATE OF CORRECTION

PATENT NO. : 4,824,671

DATED : April 25, 1989

INVENTOR(S) : Beth-Jayne Ellis; Frederick Obenchain; Raj Mehta

It is certified that error appears in the above-identified patent and that said Letters Patent is hereby corrected as shown below:

Col. 18, Line 9: change "Bacillus" to --*Bacillus*--.

Signed and Sealed this

Fifteenth Day of January, 1991

*Attest:*

HARRY F. MANBECK, JR.

*Attesting Officer*     *Commissioner of Patents and Trademarks*